(12) United States Patent  
Aerts (10) Patent No.: US 8,021,297 B2  
(45) Date of Patent: Sep. 20, 2011

(54) WEARABLE DEVICE

(75) Inventor: Steven G. E. Aerts, Oud-Heverlee (BE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 11/571,540

(22) PCT Filed: Jun. 24, 2005

(86) PCT No.: PCT/IB2005/052082  
§ 371 (c)(1),  
(2), (4) Date: Jan. 2, 2007

(87) PCT Pub. No.: WO2006/006092  
PCT Pub. Date: Jan. 19, 2006

(65) Prior Publication Data  
US 2007/0161874 A1       Jul. 12, 2007

(30) Foreign Application Priority Data

Jul. 7, 2004   (EP) ..................................... 04103218

(51) Int. Cl.  
*A61B 5/00*      (2006.01)

(52) U.S. Cl. ....................................... 600/300; 600/301

(58) Field of Classification Search .................. 600/300, 600/301; 128/903–905, 920  
See application file for complete search history.

(56) References Cited

U.S. PATENT DOCUMENTS

| 5,502,502 | A | 3/1996 | Gaskill et al. | |
|---|---|---|---|---|
| 6,513,532 | B2 * | 2/2003 | Mault et al. | 600/595 |
| 6,571,200 | B1 | 5/2003 | Mault | |
| 6,917,897 | B2 * | 7/2005 | Mork | 702/177 |
| 2002/0091329 | A1 | 7/2002 | Heikkila et al. | |
| 2008/0171919 | A1 * | 7/2008 | Stivoric et al. | 600/301 |

FOREIGN PATENT DOCUMENTS

| EP | 1238633 A1 | 9/2002 |
|---|---|---|
| JP | 06030295 | 2/1994 |
| JP | 10179560 A | 7/1998 |
| JP | 2001321370 A | 11/2001 |
| JP | 2002238877 A | 8/2002 |
| WO | 0152718 A2 | 7/2001 |

* cited by examiner

*Primary Examiner* — Sam Yao  
*Assistant Examiner* — Kai Rajan (57) ABSTRACT

A wearable device comprising at least two measuring devices (2,3,4,5,6) providing primary data, a processor (1) designed for calculating secondary data from the primary data, for calculating reference data from the primary and/or the secondary data and for comparing the reference data with at least two specific data pattern to automatically recognize an activity, and a memory (7) designed for storing the primary, the secondary data and the at least two specific data pattern each assigned to a certain activity. The activity recognition is performed by loading the primary and/or the secondary data to the processor (1), calculating the reference data, comparing the reference data with the specific data patterns, assigning the primary and/or the secondary data with the recognized activity and storing the assigned primary and/or secondary data in the memory (7).

18 Claims, 3 Drawing Sheets

FIG.4

WEARABLE DEVICE

The present invention relates to wearable devices to measure and to recognize a performed activity.

Activity monitors are used to determine data of a performed activity, which could be a fitness exercise, a medical check-up or a 24 h monitoring for medical reasons. The data could be measured directly by sensors, named primary data, or be calculated from the sensor data, named secondary data. During medical check-ups, the patient is usually instructed to perform specific activities in a laboratory environment where several sensors with skin contact can be connected by cables to analysing devices. For sport exercises, outdoor activities and/or 24 h monitoring wearable devices are used comprising a limit number of sensors and a data storage unit.

Wristwatch like wearable devices comprising a data storage/processing unit, a display, means for wireless data exchange and a number of sensors are known. The wearable devices are especially designed for specific activities such as cycling, jogging, fitness or weight management and number and kind of sensors are adapted to the specific activity. For instance, a wearable device S725 from POLAR-Germany dedicated for cycling determines the velocity/moved distance via the turning frequency of a wheel with a known circumference, not applicable for jogging. A wearable device S625X from POLAR-Germany for jogging determines the velocity via a step frequency meter not applicable for cycling. When performing different kind of activities with one wearable device, the analysis of data from non-specific sensors can only yield an averaged result, although the measured data strongly vary for different kind of activities.

The object of the present invention is to provide a wearable device able to correlate the activity data to specific activities and therefore to characterize different activities individually.

The object is achieved by a wearable device comprising at least two measuring devices providing primary data, a processor and a memory. The processor is designed for calculating secondary data from the primary data and for calculating reference data from the primary and/or secondary data as well as for comparing the reference data with at least two specific data patterns to automatically recognize an activity. The memory is designed for storing the primary, the secondary data and the at least two specific data pattern each assigned to a certain activity. The automatic recognition of a performed activity enables a direct correlation of primary and/or secondary to a certain activity and allows a data analysis for different activities individually.

One embodiment shows a wearable device designed for measuring primary and secondary data corresponding to at least two of the following data classes comprising heart rate, respiration, heat flux, body-temperature, bioelectric impedance, oxygen intake, calorie expenditure, step frequency, GPS signals, environmental temperature, vertical and horizontal acceleration, time, time intervals, velocity and skin humidity. Here, the data classes correspond to primary data measured by a specific measuring device (e.g.: heart rate measured by a heart rate monitor) and to secondary data resulting from a specific set of primary data (e.g.: for instance velocity resulting from GPS signals and time). The GPS signals denote the position coordinates of the global positioning system to identify the actual position.

Significantly different specific data pattern enable the recognition of an activity. In one embodiment the specific data pattern for jogging comprising the heart rate with minor variations over long time intervals, the velocity between 7 km/h and 25 km/h, periodic vertical and minor horizontal accelerations and a constant step frequency over long time intervals.

In another embodiment the specific data pattern for cycling comprising the heart rate mainly constant within medium time intervals, the velocity between 10 km/h and 90 km/h, discrete horizontal accelerations, negligible vertical accelerations and no step frequency.

In another embodiment the specific data pattern for water sports comprising the heart rate with minor variations over medium time intervals, the velocity below 20 km/h, low and periodic accelerations, no step frequency and high skin humidity.

In another embodiment the specific data pattern for ball games comprising the strongly varying heart rate, the velocity between 0 km/h and 30 km/h, which is strongly varying, strongly varying horizontal and vertical accelerations as well as step frequency during short time intervals.

In another embodiment the specific data pattern for fitness sports comprising the heart rate with small variations within medium time intervals, the velocity below 5 km/h, periodically varying horizontal and vertical accelerations during short time intervals and minor step frequency variation during medium time interval.

The specific data patterns comprise statistical quantities such as mean data value, highest and lowest value and data spread within time intervals and overall data spread of data classes and corresponding spectral properties, e.g Fourier transformation of data, characterising a specific activity. The number of specific data pattern is not limited to the claimed specific data pattern and can be enlarged on demand.

In one embodiment the specific data pattern comprises activity specific desired upper and lower limits for at least one data class. Desired limits of the same data class can be different for different activities. Desired limits can originate from medical reasons (for instance an upper limit for heart rate for people suffering from a heart disease) or from individual training goals.

In one embodiment the wearable device is provided with a user interface to request an activity assignment by the user in case of performing a not automatically recognized activity and means to receive the assignment made by the user in order to assign the activity data with a specific activity. For an accurate activity monitoring, it is important to compare all data sets of the same activity, therefore all stored data have to be assigned by an activity. Here, data sets denote equally assigned data from different time periods.

In another embodiment the processor calculates new specific data pattern from the user-assigned primary and/or secondary data to recognize the user-defined activity automatically for the future. The larger amount of specific data pattern increases the probability to recognize an activity and therefore improves the user convenience.

In another embodiment the user interface is designed for inserting a re-assignment of an automatically recognized activity by an user and the processor is designed for re-assigning the primary and/or secondary data.

In another embodiment the wearable device further comprises a computer interface to exchange or add data and/or specific data pattern assigned to certain activities. Activity data can be loaded to a computer for further processing, e.g. data monitoring or analysing of the effectiveness of training concepts or other purposes. Also new data comprising weight, age or height, and/or adapted activity specific data patterns can be loaded from a computer. With a larger number of specific data patterns and/or adapted patterns the probability of a successfully executed activity recognition will be larger.

New and/or adapted activity related data patterns could also comprise new and/or adapted desired data ranges and/or activity schedules according to a changed training status and/or according to medical advices.

The different additional features of the different embodiments could be realised also combined in one embodiment.

The invention also relates to an activity recognition method for a wearable device comprising the following steps:
measuring primary data as a function of time,
storing the primary and/or secondary data as a function of time,
loading the primary and/or the secondary data and the specific data patterns,
calculating reference data from primary and/or secondary data,
comparing the reference data with the specific data patterns to automatically recognize an activity,
assigning the primary and/or the secondary data with the recognized activity,
storing the assigned data,
analyzing the assigned data, and
adapting the specific data pattern according to the analyzed assigned data,
wherein an activity is recognized when a probability of correspondence between the reference data and one specific data pattern assigned to a certain activity is above a certain limit. The data analysis and the adaptation of the specific data pattern will be performed after changing the specific activity or switching off the active status of the wearable device.

In one embodiment the activity recognition method further comprises a calculation of secondary data (e.g. velocity) from the primary data.

In another embodiment the activity recognition method further comprises
sending a request to a user to assign a not recognized activity,
receiving an user-assignment,
assigning the primary and/or secondary data with the user-assignment,
calculating a new data pattern for the user-assigned activity, and
storing the user-assigned data and the new data pattern specific.

This guarantees, that there are no primary and/or secondary data, which cannot be correlated to and/or analyzed with assigned data from the same activity. A not recognized activity denotes the situation, where the probability of correspondence to the reference data is below a certain limit for all available specific data pattern.

In another embodiment the automatic recognition is interrupted for a user-defined period comprising the following steps
starting the user-defined period via the user interface,
inserting an assignment of the currently performed activity by an user,
assigning all further primary and/or secondary data with the user-assignment,
storing the user-assigned data,
leaving the user-defined period via the user interface,
loading of user-assigned data from the user-defined period,
calculating of new specific data pattern, and
storing the new specific data pattern.

Here, the wearable device will be taught to recognize certain activities, where no specific data patterns are currently available.

The assignment of data to specific activities can especially be used for monitoring sport competitions combining different kinds of sport activities such as triathlon (swimming, cycling and jogging) or any other combinations. This invention enables the analysis of specific sport activities of such competitions separately.

The same advantage can be used during 24 h monitoring for medical reasons. In this case, a correlation between measured data and every day activities can be made and critical activities can be identified with respect to desired data ranges. For not very specific or short-term daily activities the user-assignment and/or the re-assignment of activities via the user interface can be used to create an activity record of a certain period of time. With the invented wearable device it would be possible to train the daily behaviour of people with respect to identified critical activities.

In the following, the invention will be described in more details with reference to the accompanying drawings, in which
FIG. 4: flow diagram of the user-assignment of an activity The wearable device is shown in FIG. 1 in a schematic view. In this embodiment five measuring devices 2 to 6 are connected to a processor 1, e.g. to measure heart rate 2, vertical and horizontal acceleration 3, step frequency 4, time 5 and GPS signals 6. The connection between measuring device and processor can be realized by wire or wireless. The number of measuring devices and kind of measured data classes can differ from the given example in FIG. 1. The measuring devices continuously measure primary data and transfer the data to the processor 1. The processor 1 is designed for calculating secondary data from the primary data and to calculate reference data from the primary and/or secondary data, to store the primary and/or secondary data in a memory 7 and to recognize a performed activity by comparing the reference data with activity specific data pattern. The memory can be any kind of storage means comprising a shock-proofed solid-state memory.

Figure 1:
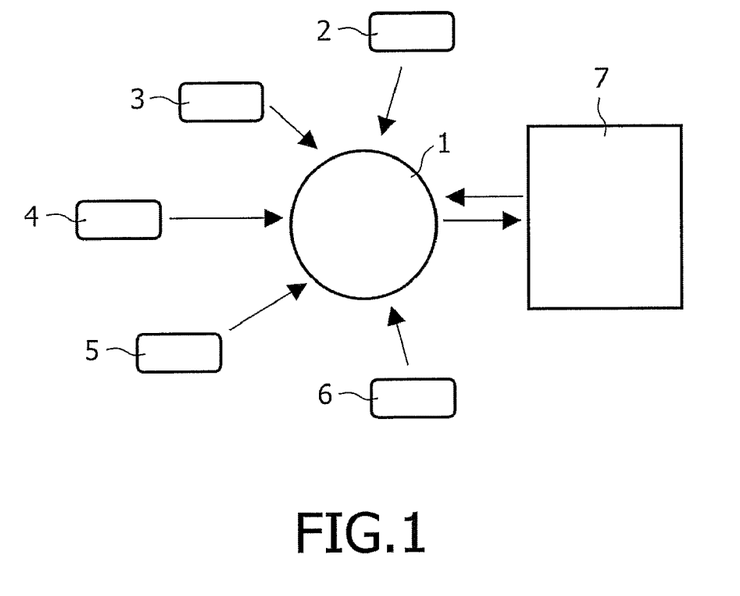
FIG. 1: shows schematic view of the wearable device

The specific data pattern comprises activity specific upper and lower values and statistical quantities such as mean data value, data spread within time intervals and overall data spread and corresponding spectral properties (e.g. Fourier transformation of data) of activity characterising data classes. The number of data classes required to identify a specific activity could be less than the number of measured primary and/or calculated secondary data classes. In another embodiment the specific data pattern can further comprise desired upper and lower limits, which do not correspond to the upper and lower values characterising a specific activity. The desired upper and lower limits serve as a guideline to perform the activity in such a way, that the corresponding data are within the desired limits. Such desired limits can be defined for any primary and/or secondary data class.

Figure 2:
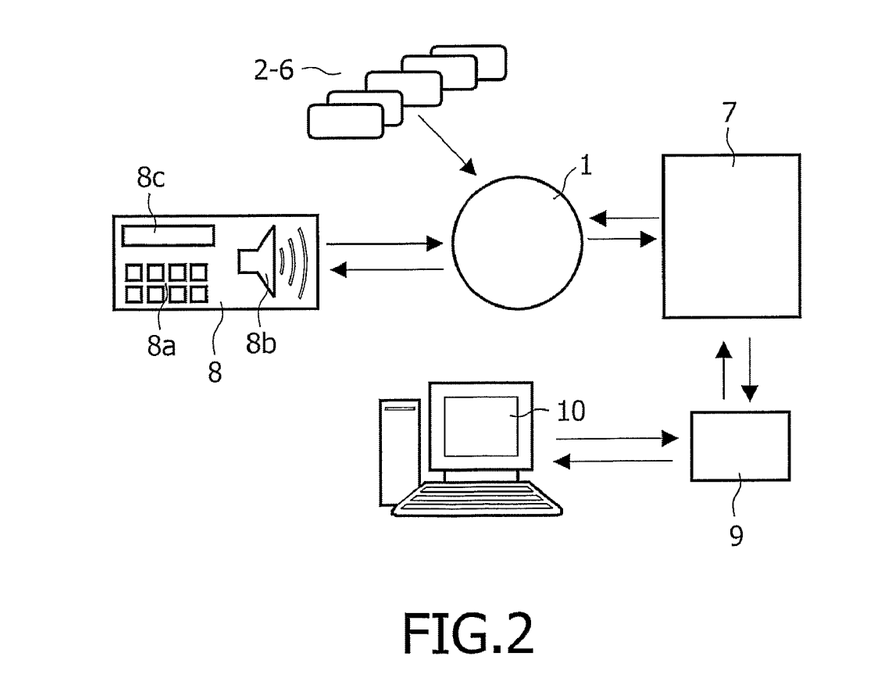
FIG. 2: shows further components of the wearable device

FIG. 2 shows another embodiment of the wearable device, which further comprises an user interface 8 designed for requesting and receiving an user-assignment of not automatically recognized activities. The request to assign a currently performed activity can be made by visual signal means via a display 8c and/or sensible and/or audible signals means 8b. The user assigns the currently performed activity and the non-assigned primary and/or secondary data will be assigned with the user-assignment. In FIG. 2 the user inserts his assignment manually via keys 8a. Alternatively, the user-assignment can be inserted via voice means or via special pens or any other manual means.

In another embodiment the user interface displays the automatic recognition of the performed activity to enable the user to correct or to overwrite the automatically made activity assignment. Since, the recognition is made by ranking of probabilities there will always be a chance to make an assignment not desired by an user. Furthermore, the overwriting is a possibility for an user to make a more specific activity assignment.

In another embodiment the user interface displays some of the current primary and secondary data and the corresponding desired upper and lower limits. The user interface further gives feedback to the user via the signal means, whether the current primary and secondary data are within the desired upper and lower limits. The user can further change the activity specific desired upper and lower limits via the user interface. In case of not automatically recognized activities, the processor 1 assigns the non-assigned primary and/or secondary data with user-made activity assignment and stores the assigned data in the memory 7. Additionally, the processor 1 calculates new specific data pattern corresponding to the user-assigned activity and stores the new specific data pattern in the memory 7. Additionally desired upper and lower limits can be inserted via the user interface for the new specific data pattern. During the next recognition procedure the formally not-recognized activity will be automatically recognized. In case of inserted new desired upper and lower limits, the corresponding specific data pattern will be adapted and stored in the memory. During the described procedure, the measuring devices 2 to 6 continuously provide primary data and transfer the measured data to the processor 1 and the processor 1 is designed for simultaneous calculation of secondary data from the measured primary data.

In another embodiment the specific data pattern comprises an activity schedule, when and how to perform a specific activity. The user interface reminds the user perform an activity according to the activity schedule.

The specific data pattern comprises important data classes with specific data properties to be compared with reference data of the same classes. An activity recognition can be difficult or impossible, if one or more measuring devices do not provide the required primary data classes to calculate the corresponding reference data. In another embodiment the processor 1 advises the user interface 8 to inform the user about missing data or data outside any reasonable range from one or more measuring devices by signal means. The user can check the operating condition of the measuring devices and can additionally insert a user-assignment of the currently performed activity.

In another embodiment the wearable device further comprises a computer interface 9 to exchange or add data and/or specific data pattern assigned to certain activities, as shown in FIG. 2. The data transfer can be executed via cable connection or by wireless means to a local computer of the user and/or to a computer located far away, for instance in a medical centre or in an escorting car. The stored primary and/or secondary data can be transferred from the memory 7 via the computer interface 9 to a computer 10 for further analysis, for example to evaluate the training effects and/or to monitor the daily variation as a function of specific activities and/or to modify the activity specific desired upper and lower limits of certain data classes. It is further possible to load personal data like weight, height and age from the computer 10 to the memory 7 via the user interface and/or computer interface 9 for calculating secondary data. It may also be possible that a weighing machine is connected to a computer, which updates weight data during data exchange with the wearable device. The computer interface is also designed for loading new or modified specific data pattern to be stored in the memory. The specific data pattern can also include an activity schedule comprising information at which time which activity and how an activity shall be performed. Such an activity schedule can also support the activity recognition.

Figure 3:
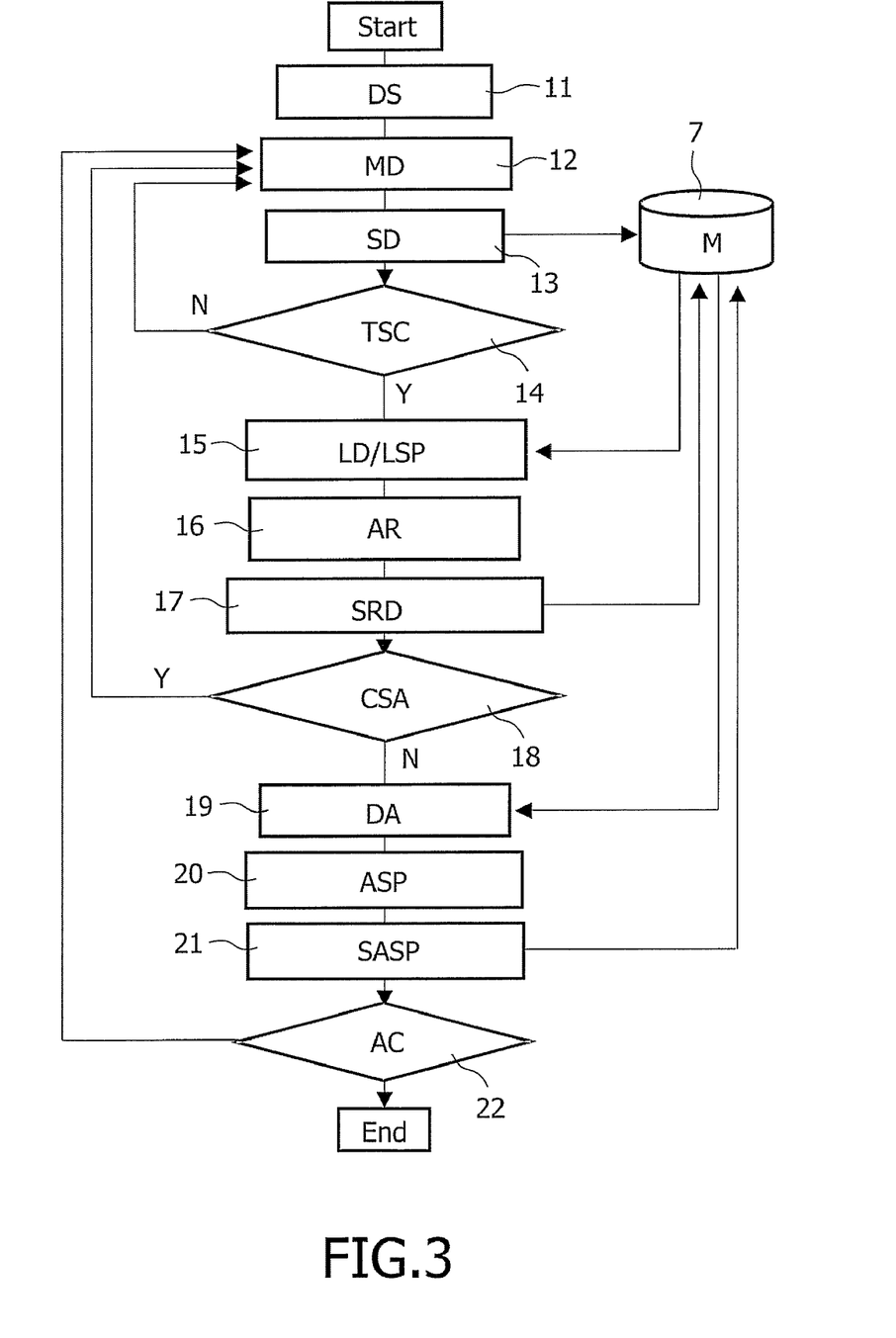
FIG. 3: flow diagram of the activity recognition method

Referring to FIG. 3, the activity recognition method of the wearable device comprises the following steps. Before entering an active status to perform the measurements a device set-up procedure checks the data connection to the present measuring devices 11. The start of the measurements can be triggered by receiving data and/or by a start command inserted via the user interface. After starting the measurements the primary data are measured periodically as long as the wearable device is in an active status 12. The primary data and/or secondary data are stored 13 in the memory 7. Before measuring new data, it is checked 14, whether the amount of data is sufficient to execute the activity recognition procedure. If the amount of data is too less, new data will be measured 12. If the amount of data is above a certain limit, the data not assigned to a specific activity and the stored specific data pattern are loaded to the processor 15. During the activity recognition procedure 16, the processor calculates reference data comprising statistical quantities such as mean data value, highest and lowest value, data spread within time intervals and overall data spread of data and corresponding spectral properties from the primary and/or secondary data. An algorithm determines the correlation probability between the reference data and the loaded specific data pattern. Since some data classes will show better correlation than others, the impact of each data class will be weighted as to form a probability scale, thus to enable comparison between activities that rely on different sets of classes. If there is a final correspondence between reference data and one specific data pattern, the activity is herewith automatically recognized and the primary and/or secondary data are assigned with the recognized activity. Thereby, different approaches can be applied to recognize a certain activity, comprising a binary approach and/or a Viterbi-like approach. All approaches are based on calculated correlation probabilities. The binary approach selects the specific data pattern with highest correlation probability (instantaneous probability IP) for a fixed time interval. The Viterbi-like approach pre-selects a reduced number of more-likely specific activities (higher IP) and continues with the calculation of instantaneous probabilities (IP) over time. From the sequence of instantaneous probabilities a cumulative probability (CP) is calculated. With increasing amount of data, the difference of the CP's for the most likely specific data pattern and the second-likely specific data pattern will increase. The procedure continues until the difference in CP between the most likely and the second likely specific data pattern is above a certain limit. There also may other procedures to recognize a specific activity.

After assigning the primary and secondary data with the recognized activity, the assigned data are stored 17 in the memory 7. In case of continued specific activity 18, the described procedure is repeated. In case of another recognized activity or a user-defined end of the current activity, the stored data assigned to the previous activity are loaded to the processor for data analysis 19. If necessary, the specific data pattern is adapted 20 and stored 21 in the memory 7. In case of further continued activities 22, the procedure continues with data measuring 12. The whole procedure stops, when the active modus of the device will be switched off.

If the primary data classes allow the calculation of secondary data, the measuring step 12 further comprises the calculation of secondary data. All further steps comprising data storage, data loading, data handling and data analyzing steps cover both, primary and secondary data.

Figure 4:
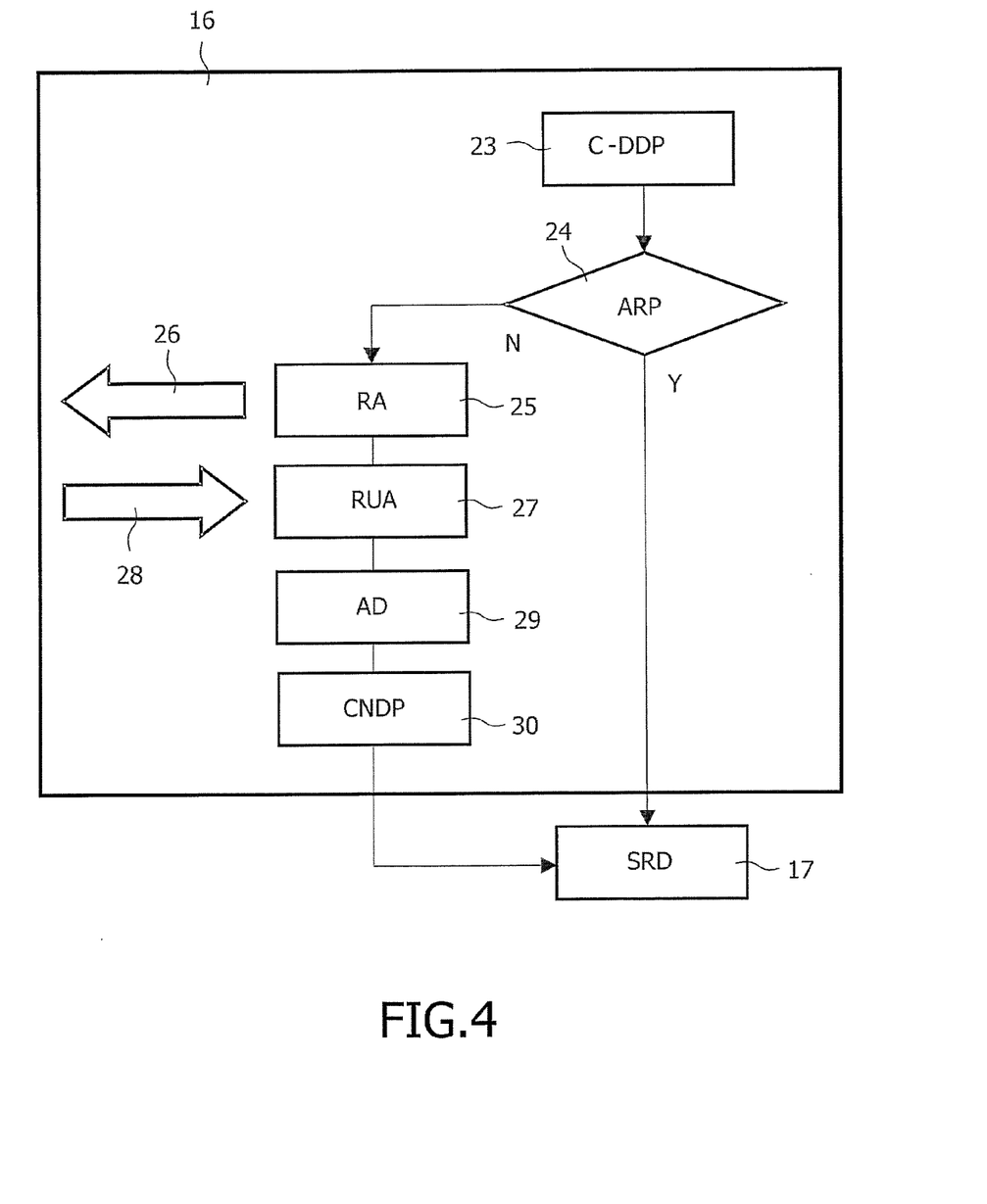

In another embodiment the activity recognition method further comprises the following steps in case of a not automatically recognized activity during the activity recognition procedure 16, as shown in FIG. 4. If the comparison of reference data with all available specific data pattern 23 does not lead to a recognition of a certain activity 24 (case "no") a request 25 is sent to the user by signal means 26 to assign the not recognized activity. Via input means 28 the user assigns the non-recognized activity. After receiving the user-assignment 27, the processor assigns the currently non-assigned data with the user-assignment 29, calculates new specific data pattern corresponding to the user-assignment 30 and stores assigned data and new calculated data pattern 17. During the following activity recognition procedure, the formally not recognized activity will now be automatically recognized.

In another embodiment the user can start a user-defined period via the user interface regardless of a successfully performed automatic activity recognition. During the user-defined period, no comparison to specific data pattern will be performed. The primary and/or secondary data will be assigned with the user-assignment as long as the user-defined period continuous. After leaving the user-defined period the processor will again perform the activity recognition procedure and new specific data pattern corresponding to the user-assignment will be calculated and stored in the memory.

The embodiments of the invention explained above represent examples of how it may be realized and are not designed to restrict the scope of the invention.

The invention claimed is:

1. A wearable device comprising:
   at least two measuring devices that provide primary data,
   a processor programmed to:
      calculate secondary data from the primary data,
      calculate reference data from the primary and/or secondary data, and
      compare the reference data with at least two specific data patterns, each data pattern corresponding to a predefined activity such that the comparing of the reference data to the data patterns automatically recognizes the corresponding predefined activity, the predefined activities including at least three of:
         jogging and the specific data pattern assigned to jogging comprises a heart rate with variations over jogging time intervals, a velocity varying between 7 km/h and 25 km/h, a periodic vertical acceleration and a constant step frequency,
         cycling and the specific data pattern assigned to cycling comprises a heart rate unvarying within cycling time intervals, a velocity varying between 10 km/h and 90 km/h, a discrete horizontal acceleration, and no step frequency,
         a water sport and the specific data pattern assigned to the water sport comprises a heart rate with variations over a water sport variation range and water sport time intervals, a velocity below 20 km/h, periodic accelerations, above normal skin humidity, and no step frequency,
         a ball game and the specific data pattern assigned to the ball game comprises a varying heart rate, a velocity varying between 0 km/h and 30 km/h, a varying horizontal and vertical acceleration during defined ball game time intervals, a strongly varying step frequency, and
         a fitness sport and the specific data pattern assigned to the fitness sport comprises a heart rate with first variations within a first fitness sport variation range and first fitness sport time intervals, a velocity below 5 km/h, a periodically varying horizontal and vertical acceleration during a second fitness sport time interval range and a varying step frequency within a second fitness sport variation during the second fitness sport time intervals; and
   a memory that stores the primary data, the secondary data and the at least two specific data patterns.

2. The wearable device according to claim 1, in which the primary and/or the secondary data correspond to at least two data classes selected from the group consisting of heart rate, respiration, heat flux, body-temperature, bioelectric impedance, oxygen intake, calorie expenditure, step frequency, GPS signals, environmental temperature, vertical and horizontal acceleration, time, time intervals, velocity, and humidity.

3. The wearable device according to claim 1, in which in response to the reference data not corresponding to one of the predefined activities, the processor is programmed to query a user to request the user to define a new activity.

4. The wearable device according to claim 1, in which the predefined activities include at least
   the water sport and the specific data pattern assigned to the water sport comprises a heart rate with variations over a water sport variation range and a water sport time interval range, a velocity below 20 km/h, periodic accelerations, above normal skin humidity, and no step frequency.

5. The wearable device according to claim 1, in which the predefined activities include at least two of:
   the water sport and the specific data pattern assigned to the water sport comprises a heart rate with variations over a water sport variation range and a water sport time interval range, a velocity below 20 km/h, periodic accelerations, above normal skin humidity, and no step frequency,
   the ball game and the specific data pattern assigned to the ball game comprises a varying heart rate, a velocity varying between 0 km/h and 30 km/h, a varying horizontal and vertical acceleration during defined ball game time intervals, a strongly varying step frequency, and
   the fitness sport and the specific data pattern assigned to the fitness, sport comprises a heart rate with first variations within a first fitness sport variation range and a first fitness sport time interval range, a velocity below 5 km/h, a periodically varying horizontal and vertical acceleration during a second fitness sport time interval range and a varying step frequency within a second fitness sport variation range during the second fitness sport time interval range.

6. The wearable device according to claim 1, in which the predefined activities include at least four of:
   jogging and the specific data pattern assigned to jogging comprises a heart rate with variations over a jogging time interval range, a velocity varying between 7 km/h and 25 km/h, a periodic vertical acceleration and a constant step frequency,
   cycling and the specific data pattern assigned to cycling comprises a heart rate unvarying within a cycling time interval range, a velocity varying between 10 km/h and 90 km/h, a discrete horizontal acceleration, and no step frequency,
   a water sport and the specific data pattern assigned to the water sport comprises a heart rate with variations over a water sport variation range and a water sport time interval range, a velocity below 20 km/h, periodic accelerations, above normal skin humidity, and no step frequency, a ball game and the specific data pattern assigned to the ball game comprises a varying heart rate, a velocity varying between 0 km/h and 30 km/h, a varying horizontal and vertical acceleration during defined ball game time intervals, a strongly varying step frequency, and a fitness sport and the specific data pattern assigned to the fitness sport comprises a heart rate with first variations within a first fitness sport variation range and a first fitness sport time interval range, a velocity below 5 km/h, a periodically varying horizontal and vertical acceleration during a second fitness sport time interval range and a varying step frequency within a second fitness sport variation range during the second fitness sport time interval range.

7. A wearable device comprising:

at least two measuring devices providing primary data, a memory which stores the primary data, secondary data and data patterns which identify previously defined activities, wherein the predefined activities include at least a water sport and the specific data pattern assigned to the water sport comprises a heart rate with variations over a water sport variation range and a water sport time interval range, a velocity below 20 km/h, periodic accelerations, above normal skin humidity, and no step frequency;

a processor programmed to:
  calculate the secondary data from the primary data,
  calculate reference data from the primary and/or secondary data,
  compare the reference data with the stored data patterns which identify the previously defined activities to automatically recognize a currently measured activity,
  in response to failing to recognize the current activity, generate a request for a definition of the unrecognized current activity,
  send the request to a user to define the unrecognized current activity, and
  in response to receiving the definition of the unrecognized activity from the user, causing the memory to store the data pattern of the current activity definition;

a user interface which displays the request for the definition of the unidentified current activity and via which the user inputs the definition of the unrecognized current activity.

8. The wearable device according to claim 7, in which the data patterns include upper and lower limits for each defined activity.

9. The wearable device according to claim 8, in which the processor is further programmed to:
  analyze the primary data and/or the secondary data stored in the memory in association with at least one of the defined activities;
  change at least one of upper and lower limits for the at least one of the defined activities in response to the analysis.

10. The wearable device according to claim 7, in which the processor calculates data patterns corresponding to activities defined by the user.

11. The wearable device according to claim 7, further comprising a computer interface which exchanges or adds data and/or specific data patterns assigned to additional activities.

12. An activity recognition method for a wearable device, wherein a processor performs the steps of
  measuring primary data as a function of time,
  calculating secondary data from the primary data,
  storing the primary and/or the secondary data as a function of time,
  loading the primary and/or the secondary data and a plurality of data patterns each corresponding to one of a plurality of predefined activities from a memory in communication with the processor, wherein the data patterns corresponding to at least one of the predefined activities have upper and lower limits and wherein the predefined activities include at least one of:
    a water sport and the specific data pattern assigned to the water sport comprises a heart rate with variations over a water sport variation range and a water sport time interval range, a velocity below 20 km/h, periodic accelerations, above normal skin humidity, and no step frequency,
    a ball game and the specific data pattern assigned to the ball game comprises a varying heart rate, a velocity varying between 0 km/h and 30 km/h, a varying horizontal and vertical acceleration during defined ball game time intervals, a strongly varying step frequency, and
    a fitness sport and the specific data pattern assigned to the fitness sport comprises a heart rate with first variations within a first fitness sport variation range and a first fitness sport time interval range, a velocity below 5 km/h, a periodically varying horizontal and vertical acceleration during a second fitness sport time interval range and a varying step frequency within a second fitness sport variation range during the second fitness sport time interval range,
  calculating reference data from the primary and/or secondary data,
  comparing the reference data with the data patterns to automatically recognize a corresponding one of the predefined activities,
  assigning the primary and/or the secondary data with the recognized predefined activity,
  storing the assigned data with the recognized predefined activity in the memory,
  analysing the assigned data corresponding to one of the predefined activities,
  modifying the data pattern corresponding to the recognized predefined activity according to the analyzed assigned data, and the adapting step includes:
    changing at least one of the upper and lower limits,
  sending a request to a user to define an activity which is not one of the recognized predefined activities,
  receiving a new activity definition from the user,
  assigning the corresponding primary and/or secondary data with a new activity definition,
  calculating a new data pattern for the new activity definition,
  storing the new activity definition and the new data pattern, and
  displaying on a display device at least one of the upper limit, the lower limit, the primary data, the secondary data, an identification of one of the predefined activities, and the data patterns.

13. The activity recognition method according to claim 12, in which the automatic recognition is interrupted for a user-defined period comprising the following steps:
  starting the user-defined period via a user interface,
  inserting a definition of a currently performed activity by a user,
  assigning further primary and/or secondary data with the user-inserted definition,
  storing the further primary and/or secondary data and the user-inserted definition,
  leaving the user-defined period via the user interface, loading further primary and/or secondary data from the user-defined period, calculating of a new data pattern from the further primary and/or secondary data, and storing the new data pattern and the user-inserted definition.

14. The activity recognition method according to claim 12, in which the data patterns corresponding to at least one of the defined activities has upper and lower limits and wherein the analysis step includes evaluating variations in the primary and/or secondary data assigned to the at least one predefined activities; and the adapting step includes modifying at least one of the upper and lower limits.

15. An activity recognition method for a wearable device, wherein a processor is programmed to perform the steps of:

measuring primary data as a function of time, calculating secondary data from the primary data, storing the primary and/or the secondary data as a function of time, loading the primary and/or the secondary data and a plurality of data patterns each indicative of a corresponding one of a plurality of predefined activities from a memory in communication with the processor, wherein the predefined activities include at least three of:

jogging and the specific data pattern assigned to jogging comprises a heart rate with variations over a jogging time interval range, a velocity varying between 7 km/h and 25 km/h, a periodic vertical acceleration and a constant step frequency, cycling and the specific data pattern assigned to cycling comprises a heart rate unvarying within a cycling time interval range, a velocity varying between 10 km/h and 90 km/h, a discrete horizontal acceleration, and no step frequency, a water sport and the specific data pattern assigned to the water sport comprises a heart rate with variations over a water sport variation range and a water sport time interval range, a velocity below 20 km/h, periodic accelerations, above normal skin humidity, and no step frequency, a ball game and the specific data pattern assigned to the ball game comprises a varying heart rate, a velocity varying between 0 km/h and 30 km/h, a varying horizontal and vertical acceleration during defined ball game time intervals, a strongly varying step frequency, and a fitness sport and the specific data pattern assigned to the fitness sport comprises a heart rate with first variations within a first fitness sport variation range and a first fitness sport time interval range, a velocity below 5 km/h, a periodically varying horizontal and vertical acceleration during a second fitness sport time interval range and a varying step frequency within a second fitness sport variation range during the second fitness sport time interval range, calculating reference data from the primary and/or secondary data, comparing the reference data with the data patterns to automatically recognize a corresponding one of the predefined activities, assigning the primary and/or the secondary data with the recognized predefined activity, storing the assigned data with the recognized predefined activity in the memory, analyzing the assigned data corresponding to one of the predefined activities, modifying the data pattern corresponding to the recognized predefined activity according to the analyzed assigned data, evaluating training data for patterns corresponding to each of a plurality of activities, defining data patterns corresponding to each of the plurality of predefined activities, and displaying on a display device at least one of the primary data, the secondary data, one of the data patterns, and an identification of one of the predefined activity.

16. The method according to claim 15, in which the predefined activities include at least two of:

the water sport and the specific data pattern assigned to the water sport comprises a heart rate with variations over a water sport variation range and a water sport time interval range, a velocity below 20 km/h, periodic accelerations, above normal skin humidity, and no step frequency, the ball game and the specific data pattern assigned to the ball game comprises a varying heart rate, a velocity varying between 0 km/h and 30 km/h, a varying horizontal and vertical acceleration during defined ball game time intervals, a strongly varying step frequency, and the fitness sport and the specific data pattern assigned to the fitness sport comprises a heart rate with first variations within a first fitness sport variation range and a first fitness sport time interval range, a velocity below 5 km/h, a periodically varying horizontal and vertical acceleration during a second fitness sport time interval range and a varying step frequency within a second fitness sport variation range during the second fitness sport time interval range.

17. An activity recognition method for a wearable device, wherein a processor performs the steps of:

measuring primary data as a function of time, calculating secondary data from the primary data, storing the primary and/or the secondary data as a function of time, loading the primary and/or the secondary data and a plurality of data patterns each indicative of a corresponding to one of a plurality of predefined activities from a memory, wherein the predefined activities include at least three of:

jogging and the specific data pattern assigned to jogging comprises a heart rate with variations over a jogging time interval range, a velocity varying between 7 km/h and 25 km/h, a periodic vertical acceleration and a constant step frequency, cycling and the specific data pattern assigned to cycling comprises a heart rate unvarying within a cycling time interval range, a velocity varying between 10 km/h and 90 km/h, a discrete horizontal acceleration, and no step frequency, a water sport and the specific data pattern assigned to the water snort comprises a heart rate with variations over a water sport variation range and a water sport time interval range, a velocity below 20 km/h, periodic accelerations, above normal skin humidity, and no step frequency, a ball game and the specific data pattern assigned to the ball game comprises a varying heart rate, a velocity varying between 0 km/h and 30 km/h, a varying horizontal and vertical acceleration during defined ball game time intervals, a strongly varying step frequency, and a fitness sport and the specific data pattern assigned to the fitness sport comprises a heart rate with first variations within a first fitness sport variation range and a first fitness sport time interval range, a velocity below 5 km/h, a periodically varying horizontal and vertical acceleration during a second fitness sport time interval range and a varying step frequency within a second fitness sport variation range during the second fitness sport time interval range, calculating reference data from the primary and/or secondary data, comparing the reference data with the data patterns to automatically recognize a corresponding one of the predefined activities, assigning the primary and/or the secondary data with the recognized predefined activity, storing the assigned data with the recognized predefined activity in the memory, analyzing the assigned data corresponding to one of the predefined activities, modifying the data pattern corresponding to the recognized predefined activity according to the analyzed assigned data, and displaying on a display device at least one of the primary data, the secondary data, one of the data patterns, and an identification of one of the predefined activity, in which the comparing step includes:

calculating a correlation probability of the reference data and the data patterns of the predefined activities.

18. The method according to claim 17, in which the predefined activities include at least two of:

the water sport and the specific data pattern assigned to the water sport comprises a heart rate with variations over a water sport variation range and a water sport time interval range, a velocity below 20 km/h, periodic accelerations, above normal skin humidity, and no step frequency, the ball game and the specific data pattern assigned to the ball game comprises a varying heart rate, a velocity varying between 0 km/h and 30 km/h, a varying horizontal and vertical acceleration during defined ball game time intervals, a strongly varying step frequency, and the fitness sport and the specific data pattern assigned to the fitness sport comprises a heart rate with first variations within a first fitness sport variation range and a first fitness sport time interval range, a velocity below 5 km/h, a periodically varying horizontal and vertical acceleration during a second fitness sport time interval range and a varying step frequency within a second fitness sport variation range during the second fitness sport time interval range.

* * * * *